US006779379B2

(12) United States Patent
Grob et al.

(10) Patent No.: US 6,779,379 B2
(45) Date of Patent: Aug. 24, 2004

(54) METHOD AND DEVICE FOR VAPORIZATION INJECTION

(75) Inventors: Konrad Grob, Fehraltorf (CH); Fausto Munari, Milan (IT); Paolo Magni, Besana Brianza (IT)

(73) Assignee: Thermo Finnigan Italia S.p.A., Rodano (IT)

( * ) Notice: Subject to any disclaimer, the term of this patent is extended or adjusted under 35 U.S.C. 154(b) by 36 days.

(21) Appl. No.: 09/898,505

(22) Filed: Jul. 3, 2001

(65) Prior Publication Data

US 2002/0020209 A1 Feb. 21, 2002

(30) Foreign Application Priority Data

Jul. 19, 2000 (IT) ..................................... MI2000A1634

(51) Int. Cl.[7] ................................................. G01N 1/00
(52) U.S. Cl. .................... 73/23.41; 73/23.35; 73/23.39; 73/23.4; 95/87; 95/89
(58) Field of Search ............................ 73/23.41, 23.35, 73/23.39, 23.4; 95/87, 89

(56) References Cited

U.S. PATENT DOCUMENTS

| 4,628,726 A | * 12/1986 | Heikkila et al. ............ 73/61.53 |
| 5,672,810 A | 9/1997 | Shibamoto |
| 5,783,742 A | 7/1998 | Ueda et al. |
| 6,203,597 B1 | * 3/2001 | Sasano et al. .................. 95/87 |
| 6,451,614 B1 | * 9/2002 | Grob et al. .................. 436/161 |

FOREIGN PATENT DOCUMENTS

| EP | 0051778 A | 5/1982 |
| EP | 0461438 A | 12/1991 |
| EP | 0510511 A | 10/1992 |
| EP | 0551847 A | 7/1993 |
| EP | 1 063523 A | 12/2000 |
| WO | WO 9428409 A | 12/1994 |
| WO | WO 0133209 A | 5/2001 |

OTHER PUBLICATIONS

K. Grob, "Injection Techniques in Capillary GC", Analytical chemistry., vol. 66, No. 20, Oct. 15, 1994, pp. 1990a–1919a, XP002181891, American Chemical Society. Columbus., US ISSN: 0003–2700 * p. 1012A; fiqure 4*.

* cited by examiner

*Primary Examiner*—Hezron Williams
*Assistant Examiner*—André K. Jackson
(74) *Attorney, Agent, or Firm*—Gibbons, Del Deo, Dolan, Griffinger & Vecchione

(57) ABSTRACT

The invention concerns a device for vaporizing injections of samples into a gas chromatography analysis device, comprising a vaporization chamber elongated lengthways and heated, as well as a syringe equipped with a needle, the device being of the type in which the introduction of the sample is carried out without prior vaporization of the sample within the needle, and also foresees at least one stop and vaporization means for the liquid inside the vaporization chamber. To improve the conditions of vaporization and the transfer of the sample, the distance between the free end of the needle and the stated stop and vaporization means for the liquid is greater than 55 mm (FIG. 1).

24 Claims, 3 Drawing Sheets

METHOD AND DEVICE FOR VAPORIZATION INJECTION

BACKGROUND OF THE INVENTION

Field of the Invention

The present invention relates to a device for vaporization injection into a gas chromatography analysis device.

Several methods are known of injecting and vaporizing samples into a gas chromatography analysis device, in which the samples formed by the substance to be analyzed and a solvent, are injected by means of syringes equipped with a needle into the vaporization chambers generally in the form of heated cylinders, in which the said samples vaporize and then pass into the capillary column for analysis. The type of injection can be split or splitless, depending on whether the sample is passed only in the part through the column ("split mode") or in its entirety ("splitless mode").

In each case, it is important that the sample vaporizes in an optimum manner and in its entirety within the vaporization chamber, in a position above the column entrance where it is temporarily held before being transferred to the column for analysis.

In the known vaporization methods, it is provided to use long needles in order to inject the sample into the centre or at the base of the vaporization chamber. In particular, for the splitless method, in accordance with the current technique, the needles need to reach a certain point so that the vaporization centre occurs a little above the column entrance. This is to avoid sample loss occurring towards the top of the chamber.

In these systems, the vaporization chamber is completely heated to a temperature above the vaporization temperature of the sample to be analyzed, and the sample injected through the needle is vaporized immediately.

Two alternative techniques are used for vaporizing the samples. The first commonly used technique foresees a so-called flash vaporization of the sample within the chamber, with preheating and pre-vaporization of the sample within the needle. The time spent by the needle within the chamber increases the temperature of the same and this causes a violent evaporation of the solvent present within the sample, which causes the liquid to be expelled from the needle at a high pressure; on leaving the needle, the liquid is broken up into tiny droplets forming an aerosol so that the droplets are slowed down and can therefore be immediately vaporized. The drawbacks of this technique are connected to the fragility of the unavoidably long needles which have to be used for this type of injection, and to the discrimination phenomenon, mainly because a high boiling part of the sample may remain inside the needle.

As a result, conventional vaporization chambers normally are shorter than ideal dimensions, with much smaller internal volumes than desirable. Frequently it is also possible to register sample losses through the head of the chamber and the purge of the septum due to the "overflow" phenomenon. The second alternative technique, so-called "cold-fast injection", foresees the insertion of the needle and the expulsion of the liquid within fractions of a second to eliminate or substantially reduce the phenomenon of sample heating in the needle and the consequent discrimination.

However, this technique presents other drawbacks, for example it may only be carried out using automatic samplers and not manually, as it is not possible for an operator to manually carry out all the movements necessary for this technique which are required to be carried out in a time of the order of 500 milliseconds or less. As a consequence, the vaporization of the sample in the injector is substantially different according to whether the injection was carried out manually or automatically, and the analysis results gathered according to the two methods are not homogenous.

OBJECTS AND SUMMARY OF THE INVENTION

The present invention originates from the discovery made by one of the inventors according to which, if the injection of the sample is carried out without using the "thermal spray" technique, or if the injection is carried out avoiding the vaporization of the sample in the needle, the ejected liquid forms a liquid jet or band, which travels a long way across the chamber in a practically unaltered form without touching the chamber walls, as close to these walls it is repelled by the vaporization of small quantities of solvent.

Based on these observations, it has been possible to create a vaporization injection device which eliminates the drawbacks of the known techniques, and allows a highly reliable analysis even of samples of considerable volume. It has been ascertained, and this constitutes the base of the present invention, that the injection samples without vaporization within the needle, allows to overcome the previous limitations due to the fact that the sample had to be injected close to the base of the vaporizing chamber or close to a stop and vaporization means for the liquid, such as a pack or another obstacle. Therefore, the invention concerns a vaporization injection device of the type without vaporization within the needle, in which the distance from the point or free end of the needle to the stop and vaporization means is much longer than that provided by the prior technique, and in particular greater than 55 mm and preferably greater than 80 mm.

The minimum value quoted above has been set in order to allow the vaporization injection also of large quantities of samples in a reliable manner, without recording "overflow" losses as described above.

In order to obtain a sample delivery as a liquid band it is fundamental that the inside of the needle is cold, or at a temperature below the boiling point of the solvent at the pressure within the same needle, and that for the entire duration of the injection.

A good method to obtain this is to use a very short needle, which can now be used as the foreseen distance from the point of the needle to the stop means and vaporization of the liquid is longer than above. Any minimal vaporization before the injection in such a short needle does not substantially influence the emission of the sample as a jet or band.

However, it is possible to take other precautions to guarantee this type of emission under all operating conditions. These precautions, which may be applied singularly or together, essentially consist of:

reduction of the internal diameter of the needle, to reduce the quantity of sample within the same needle before emission starts,
 maintenance of the injection head, and therefore of the needle, at a relatively low temperature—by cooling or simply ambient thermal exchange—in a manner that the temperature of the needle remains below that of vaporization of the solvent before and during injection,
 protection of the needle with a thermal insulating covering.
 forming the needle in a thermal insulating material.

The invention will be now described in a detailed manner with reference to particular embodiments of the same, illustrated as examples in the annexed drawings.

BRIEF DESCRIPTION OF THE DRAWINGS

With reference to FIG. 1, the injector body 11 is attached to a vaporization chamber 6, above which is positioned a septum 1 fixed to the injector by a retainer 2.

DESCRIPTION OF THE PREFERRED EMBODIMENTS

Figure 1:
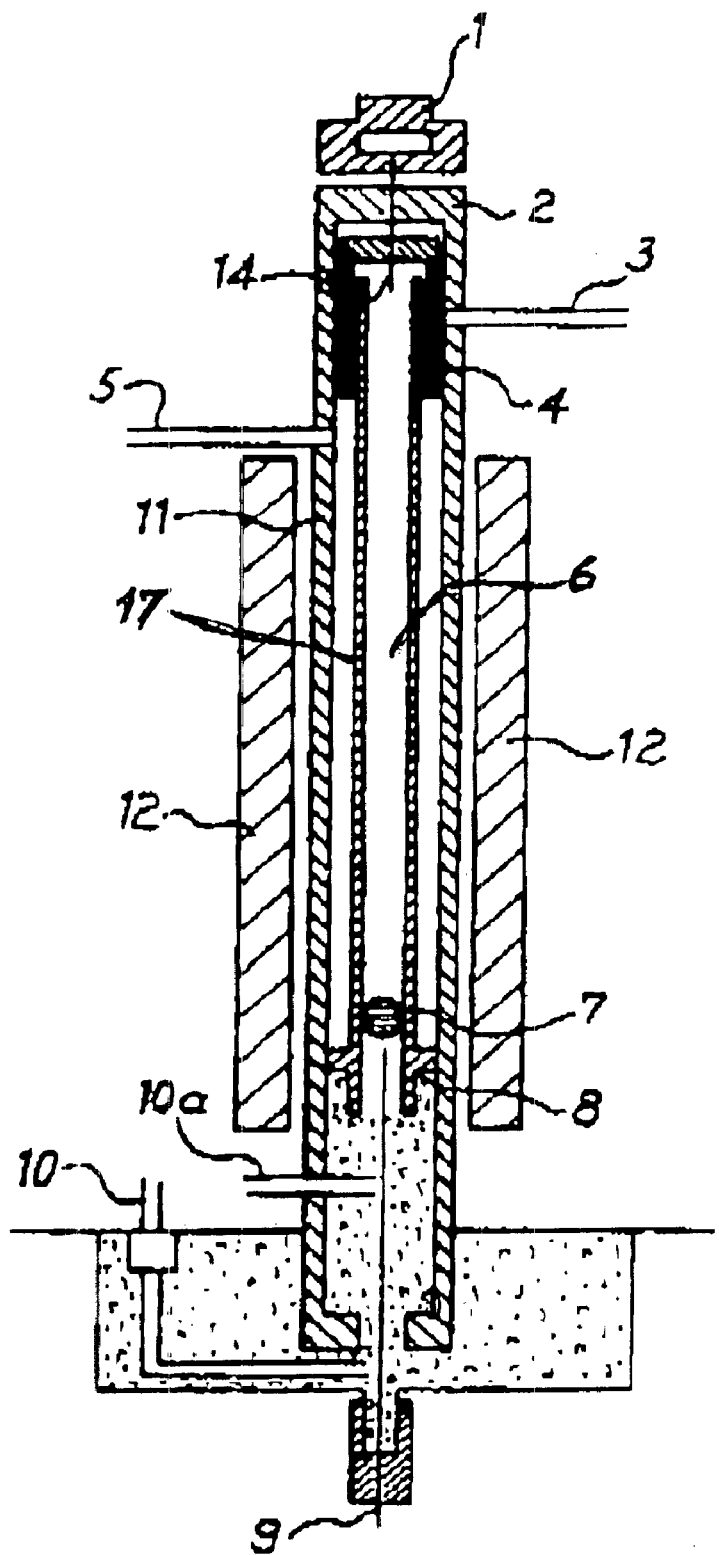
FIG. 1 is a schematic representation of a vaporization injector formed and working in accordance with the principles of the invention.

The vaporization chamber 6 is preferably only heated in the lower portion by well known heating elements 12, while the upper portion, closed by a cup 4, is preferably cooled or at least not heated.

The injector also includes a port 5 for the introduction of the carrier gas and a port 3 used during septum purging operations by the carrier gas. The vaporization chamber 6 is fixed to the injector body by means of a retainer 8 which is preferably in metal. The ducts 10 and 10a schematically indicate the possible position of the splitting lines. The sample, made up according to the known techniques, is introduced into the chamber via a micro-syringe, the needle 14 of which, preferably having reduced dimensions in comparison to those of a conventional needle, perforates the septum 1 to reach a predetermined point in the chamber, and injects the sample in a liquid state as a band-like jet which travels across the remaining part of the strongly heated vaporization chamber with such a speed that the heat transfer and the resulting vaporization are negligible. In any case, the liquid band is repelled by a sort of "cushioning" effect caused by the vaporization of a tiny quantity of solvent on the chamber walls, in such a way that this band remains unaltered as it crosses the said chamber lengthways and holds its configuration even in the case the chamber is curved.

In particular, the sample is injected in correspondence to or close to the cooled or unheated upper portion of the vaporization chamber, through a needle 14 of reduced length, for example, so as to penetrate into the chamber to a depth of not more than 30 mm.

For the vaporization, the liquid sample is transferred onto a stop and vaporization means, for example, a pack in glass wool or deactivated fused silica or otherwise a material for packed columns, indicated in the figures with the reference 7. Alternatively the sample is stopped by an obstacle or a trap between obstacles, as happens for example in the "laminar liner" supplied by the company Restek.

The position of the said pack or obstacles inside the chamber determines the central point of the sample vaporization and so allows to avoid that the droplets of liquid enter into the column 9 or directly pass into the splitting channel.

As shown, as the needle has to enter the vaporization chamber to only a short length (corresponding to the chamber cooled or unheated portion) it is sufficient to use short needles which allow the injections, in the form of a band of liquid, even in the case of much slower manual injections, or using an auto-sampler which imitates manual injections.

And again according to the invention, by eliminating the problem of the long needles necessary to reach the base of the chamber, it is possible to use a chamber of longer length to increase the chamber capacity, and as a result to eliminate the loss caused by "overflow".

Depending on a preference factor, the needles employed based on the invention may have a length of less than 30 mm, favorably less than 20 mm. Alternatively these needles may be longer but introduced only partly Into the vaporization chamber.

Preferably the internal diameter of the needle should be very small to increase the exit speed of the sample, and at the same time reduce the quantity of the sample present within the needle. For example, the needle should have an internal diameter of less than 0.13 mm.

In compatibility with the characteristics of the device, in particular with the septum employed, also the external diameter of the needle should preferably be minimized to ensure that the thermal capacity of the needle is reduced. In this way, the needle should preferably have a very thin metal wall and eventually be externally lined with a thermal insulation covering in such a way as to reduce the heating of the needle to a minimum. Alternatively, the needle may be formed completely of a thermal insulating polymeric material.

Figure 3:
FIG. 3 is a schematic representation of a Merlin valve.

Depending on a preference factor, the septum 1 may be substituted with a Merlin valve 18 (FIG. 3). The septum 1 and the Merlin valve 18 should preferably be of the same dimension in order to be interchangeable. In particular, the use of the Merlin valve 18 would avoid contamination problems by silicons contained in the septums normally employed.

Figure 4:
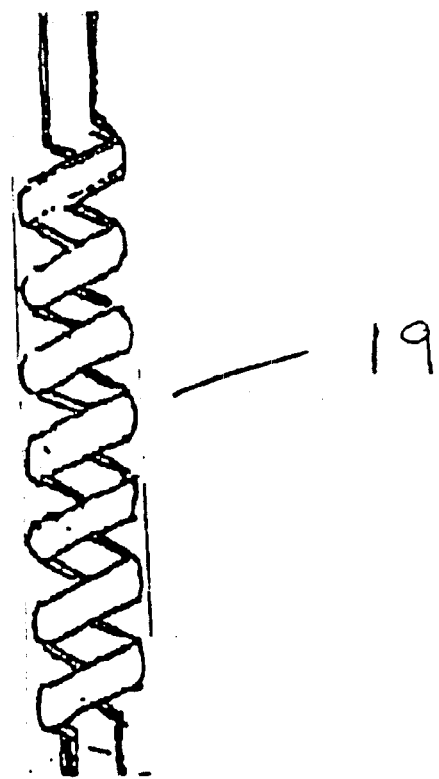
FIG. 4 is a schematic representation of a coiled vaporization chamber.

According to another preference factor, the vaporization chamber has a length of more than 10 cm, preferably more than 15 cm. In particular cases said chamber can have a length of more than 30 cm. This chamber should be coiled as shown in the coiled chamber 19 of FIG. 4.

The possibility of using a much longer vaporization chamber compared to conventional ones offers important advantages. In fact, the "overflow" observed when the sample is injected in the splitless mode, into conventional chambers having a length of about 80 mm, represents one of the main causes of analysis error because the volume of vapor generated by sample vaporization is large in relationship to the volume available inside the chamber.

Theoretically it would be possible to increase the volume of the vaporization by widening the diameter, but this could cause an increased remixing of vapors inside it and a much greater dilution by the carrier. Furthermore, it happens that the carrier speed inside a chamber having a larger diameter is normally too low to obtain an efficient transfer of the vapors into the column. As a consequence, it is considered more convenient to increase the capacity of the chamber, in which the sample vapors to be analyzed are temporarily held, lengthways more than in the width.

The operations of taking and introducing the sample into the vaporization chamber 6 can be carried out manually or by use of an automatic sampler. It has been recorded that a sample exit speed from the needle equal to about 10 m/s, which is normally achieved manually, is sufficient to transfer the liquid to a pack at a distance greater than 20 cm without generating appreciable vaporization. In fact, if the liquid sample exits the needle at an average speed of 10 m/s and for example, covers a distance of 10 cm in about 10 milliseconds, as the evaporation of 2 $\square$l of sample in a solvent in a chamber at a temperature of about 250° C. requires from about 100 milliseconds to several seconds, it is clear that this period is too short to initiate evaporation of a significant part of the sample or the solvent.

If desired, the invention can also be carried out according to the injection technique which foresees the introduction of an empty needle, or according to a technique which foresees a vaporization of only the solvent in the needle before the injection, in order to cool it to the desired injection temperature.

To be able to inject large quantities of sample the capacity of the chamber is increased in order to eliminate the external "dead volume", which allows an enhancement of the "pulse pressure" effect which occurs mainly in automatic mode during the vaporization injection.

In particular the liner 17 can be made of metallic material such as "silcosteel" and fixed by a metal retainer 8 at the base of the injector body 11.

With these kinds of precautions, it is possible for example to introduce up to 10 □l of hexane.

The device of this invention may be used to carry out gas chromatography analyses in split or splitless mode.

The analyses are then carried out as usual, the sample is vaporized by means of high temperature in the lower portion of the chamber and is dragged by a carrier which is introduced through the port 5; any splitting functions are obtained from channel 10 or 10a.

The analyses may eventually be controlled by a special software packet for the regulation of the carrier pressure based on other parameters such as diameter and length of the vaporization chamber, the quantity of samples, the solvent nature, etc.

The device also comprises all parts normally to be found in analog systems and not interfering with the new aspects of vaporization injection of this invention.

Figure 2:
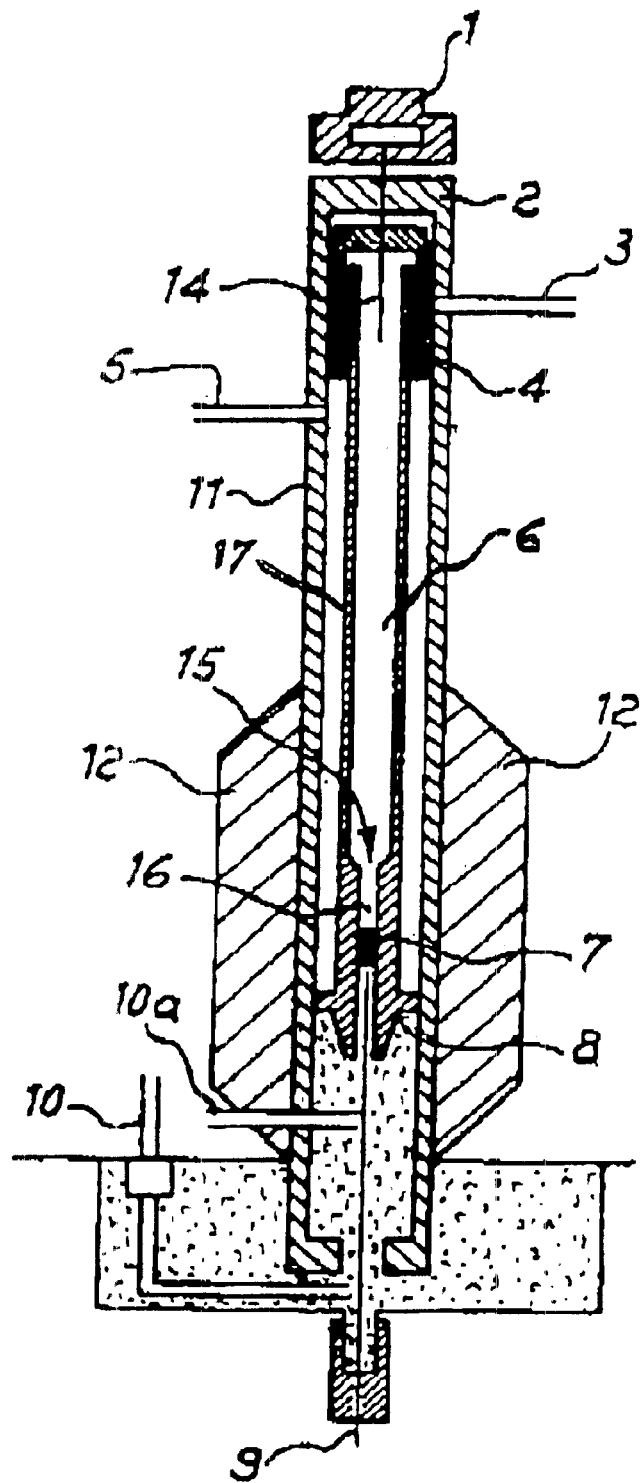
FIG. 2 is a schematic representation of a modified injector, in order to make better use of the advantages originated from the invention.

In FIG. 2, where the same reference numbers have been used to indicate the same or similar components to those illustrated in FIG. 1, is shown a type of vaporization injector especially developed to optimize the invention's advantages.

As opposed to the injector in FIG. 1, that in FIG. 2 has a heating element 12 positioned much lower towards the base of the chamber 6 so as to achieve the maximum heating effect, enough to vaporize all the sample to be found at the base of the chamber, while the parts of the same above this zone are heated only in sufficient measure to create the "cushioning" effect described earlier, which guarantees the maintenance of the liquid band.

The chamber 6 "liner" 17 of FIG. 2, as opposed to that in FIG. 1, shows a funneled restriction at the base, as indicated with 15, which continues towards the base with a narrow channel 16. The stop and vaporization means 7 is placed within the narrow channel 16, for example in glass wool, immediately above the column entrance 9.

This particular configuration allows the liquid band to be conveyed into the obstacle zone 7, where the solvent and the more volatile composites initially vaporize and expand upwards towards the larger part of the chamber. The vaporization of the solvent momentarily cools the narrower zone which then successively reaches the operating temperature. Then the solutes, which are held in the narrower zone, evaporate forming a small volume of vapor, which can be carried into the column with maximum efficiency.

Furthermore, in the narrower zone the speed of the carrier gas is higher and causes a rapid transfer into the column, avoiding the degradation of the unstable solutes and any retention or adsorption into the glass wool 7. The solvent and the volatile solutes evaporated with the solvent are so transferred more easily into the column, notwithstanding the relatively low temperature in the upper part of the chamber, as they are only volatile components.

What is claimed is:

1. A device for vaporization injection of samples into a gas chromatography analysis instrument, comprising an elongated vaporization chamber having a lower portion that is constantly heated and having an upper portion, a syringe equipped with a needle that is arranged to inject a sample liquid through a tip of the needle to be released in a form of a liquid band into the upper portion where the released infected sample is maintained in the form of the liquid band, the device being configured to render vaporization of the sample liquid within the needle negligible, and further containing means for stopping and vaporizing the released sample liquid within the lower portion of the vaporization camber and above a column entrance, characterized in that a distance between the tip of the needle and the means for stopping and vaporizing the sample liquid above the column entrance is greater than 55 mm.

2. A device according to claim 1, characterized in that said distance is greater than 80 mm.

3. A device according to claim 1, characterized in that said needle extends into the vaporization chamber for length less than 30 mm.

4. A device according claim 1, characterized in that the internal channel of said needle has a diameter of less than 0.13 mm.

5. A device according to claim 1, in which the upper portion of said vaporization chamber is cooled or unheated.

6. A device according to claim 1, in which the external wall of said needle is covered by a thermal insulating material.

7. A device according to claim 1, in which said needle is completely formed in a thermal insulating polymer.

8. A device according to claim 1, in which the complete length of said vaporization chamber is greater than 10 cm.

9. A device according to claim 8, in which the complete length of said vaporization chamber is greater than 15 cm.

10. A device according to claim 1, in which said vaporization chamber is coiled.

11. A device according to claim 1, in which said vaporization chamber is formed in metal.

12. A device according to claim 11, in which the stated vaporization chamber is formed in "silcosteel".

13. A device according to claim 1, in which a conventional septum or a Merlin valve are able to be alternately mounted on the injector head.

14. A device according to claim 1, characterized in that said vaporization chamber has a restriction in its lower part containing said stop and vaporization means.

15. A device according to claim 14, characterized in that said restriction is connected to the upper part of the chamber by a funneled wall.

16. A device according to claim 1, characterized in that heating means for the vaporization chamber are provided operating at the vaporization temperature of the sample in correspondence to a restriction, and at a lower temperature in the upper part of the chamber than that in the lower portion of the chamber.

17. A vaporization method for a sample injected into a constantly heated vaporization chamber of a gas chromatography analysis instrument, characterized in that said sample is injected through a tip of a needle of a syringe into an upper portion of said vaporization chamber and is released from the tip of the needle in a form of a liquid band crossing said vaporization chamber from the upper portion where the released sample is maintained in the form of the liquid band, to a lower portion of the vaporization chamber, and that said released sample is stopped by liquid stop means that is positioned above a column entrance and said released sample is vaporized in the lower portion of the heated chamber, a distance between the tip of the needle and the liquid stop means being greater than 55 mm.

18. A method according to claim 17, in which said needle is inserted into said chamber for a length not greater than 30 mm.

19. A device according to claim 1, in which heating means for the vaporization chamber are provided so as to achieve a maximum heating effect to vaporize all the sample towards the base of the chamber, and a lower temperature in the upper portion of the chamber.

20. A method according to claim 17, in which the lower portion of the chamber is heated to vaporize all the sample, and the upper portion of the chamber is operated at a lower temperature than that of the lower portion of the chamber.

21. A device for vaporization injection of a sample into a gas chromatography analysis instrument, comprising an elongated vaporization chamber, a syringe equipped with a needle to inject a liquid sample, a stop and vaporization means for arresting the injected liquid sample and for vaporizing same within the elongated vaporization chamber, means for heating at least part of the elongated vaporization chamber to a temperature above a vaporization temperature of the sample while a further part of the elongated vaporization chamber is maintains the injected liquid in a form of a liquid, a distance between a tip of the needle and the stop and vaporization means being greater than 55 mm.

22. A device as in claim 21, further composing heating means for the elongated vaporization chamber, the heating means being arranged and configured to vaporize all the sample towards a base of the elongated vaporization chamber and provide a temperature in an upper portion of the vaporization chamber that is lower than at a base.

23. A vaporization method for a sample injected within a vaporization chamber of a gas chromatography analysis instrument, comprising heating at least a lower portion of the vaporization chamber to a temperature above a vaporization temperature of a sample to be analyzed, injecting through a tip of a needle of syringe the sample in correspondence with or in proximity of an upper portion of the vaporization chamber, releasing the sample from the tip of the needle in form of a liquid band crossing the vaporization chamber from the upper portion where the released sample is maintained in the form of the liquid band to the lower portion, stopping the released sample by liquid stop means that is positioned above a column entrance; and vaporizing the released sample in the lower portion of the vaporization chamber, a distance between the tip of the needle and the liquid stop means being greater than 55 mm.

24. A vaporization method as in claim 23, wherein the heating of the lower portion of the chamber includes heating to vaporize all of the sample, further comprising operating at a lower temperature in an upper portion of the vaporization chamber than that within the lower portion of the vaporization chamber.

\* \* \* \* \*

UNITED STATES PATENT AND TRADEMARK OFFICE
CERTIFICATE OF CORRECTION

PATENT NO. : 6,779,379 B2
DATED : August 24, 2004
INVENTOR(S) : Konrad Grob

It is certified that error appears in the above-identified patent and that said Letters Patent is hereby corrected as shown below:

Column 6,
Line 14, please change "camber" to read -- chamber --.

Signed and Sealed this

Tenth Day of May, 2005

JON W. DUDAS
*Director of the United States Patent and Trademark Office*